United States Patent
Coufal et al.

(10) Patent No.: US 6,870,050 B2
(45) Date of Patent: Mar. 22, 2005

(54) METHOD FOR THE PRODUCTION OF MELAMINE

(75) Inventors: Gerhard Coufal, Leonding (AT); Hartmut Bucka, Eggendorf (AT); Faramarz Bairamijamal, Linz (AT)

(73) Assignee: Agrolinz Melamin GmbH, Linz (AT)

( * ) Notice: Subject to any disclaimer, the term of this patent is extended or adjusted under 35 U.S.C. 154(b) by 0 days.

(21) Appl. No.: 10/344,190

(22) PCT Filed: Jul. 26, 2001

(86) PCT No.: PCT/EP01/08648

§ 371 (c)(1), (2), (4) Date: Sep. 25, 2003

(87) PCT Pub. No.: WO02/12206

PCT Pub. Date: Feb. 14, 2002

(65) Prior Publication Data

US 2004/0049034 A1 Mar. 11, 2004

(30) Foreign Application Priority Data

Aug. 7, 2000 (AT) .......................................... A 1363/00

(51) Int. Cl.⁷ ...................... C07D 251/60; C07D 251/62
(52) U.S. Cl. ...................................... 544/201; 544/203
(58) Field of Search .................................. 544/201, 203

(56) References Cited

U.S. PATENT DOCUMENTS 4,565,867 A    1/1986   Thomas et al.

2001/0005751 A1    6/2001    Coufal

FOREIGN PATENT DOCUMENTS

| AT | 289 133 | 4/1971 |
|---|---|---|
| AT | 402 294 B | 3/1997 |
| DE | 1 279 023 | 10/1968 |
| DE | 35 00 188 A1 | 7/1985 |
| EP | 0 747 366 A2 | 12/1996 |
| WO | WO 97/20826 | 6/1997 |
| WO | WO 98/04533 | 2/1998 |
| WO | WO 99/38852 | 8/1999 |
| WO | WO 00/29393 | 5/2000 |

OTHER PUBLICATIONS

International Search Report of PCT/EP01/08648, dated Nov. 28, 2011.

International Preliminary Examination Report of PCT/EP01/08648, dated Feb. 22, 2002.

Primary Examiner—Venkataraman Balasubramanian
(74) Attorney, Agent, or Firm—Christie, Parker & Hale, LLP

(57) ABSTRACT

A process for preparing melamine by pyrolysis of urea in a high-pressure process, in which urea is reacted together with $NH_3$ to give melamine and the melamine melt formed is fed together with further urea to a cooling reactor, with the melt being cooled to a temperature which is 1–50° C., preferably 1–30° C., above the melting point of the melamine, which is dependent on the prevailing $NH_3$ pressure. Introduction of $NH_3$ in countercurrent drives out the $CO_2$ formed, after which the melamine melt is worked up in any appropriate way.

18 Claims, 1 Drawing Sheet

METHOD FOR THE PRODUCTION OF MELAMINE

CROSS-REFERENCE TO RELATED APPLICATION

This application is a National Phase Patent Application of International Application Number PCT/EP01/08648, filed on Jul. 26, 2001, which claims priority of Austrian Patent Application Number A 1363/00, filed Aug. 7, 2000.

The invention relates to the preparation of melamine by pyrolysis of urea in a high-pressure process using reactors connected in series.

BACKGROUND OF THE INVENTION

In the high-pressure processes for preparing melamine, urea is reacted in an endothermic liquid-phase reaction to form melamine. The liquid melamine additionally contains, depending on the pressure and temperature conditions in the reactor, variable amounts of dissolved $NH_3$ and $CO_2$ and also condensation by-products and unreacted urea. The resulting melamine, which is under a high $NH_3$ pressure, is subsequently solidified by, for example, quenching with water or with ammonia, by sublimation with subsequent desublimation or by depressurization under particular conditions. The reactor used is customarily a single apparatus of the stirred tank type.

A significant problem in the preparation of melamine from urea is that the urea used is not reacted completely and also that by-products which subsequently have to be converted into melamine by means of costly and complicated work-up steps are formed in the reactors customary in the prior art. For example, it is known from WO97/20826 that pure melamine can be obtained when the melamine is, prior to solidification, cooled to temperatures which are just above the respective melting point of the melamine, which depends on the prevailing $NH_3$ pressure. The cooling of the melamine prior to solidification is carried out by addition of $NH_3$ or by means of heat exchangers.

SUMMARY

It has surprisingly been found that cooling of melamine prior to solidification can be achieved by the addition of a small amount of urea which is simultaneously converted into melamine in an endothermic reaction. Cooling occurs with the formation of further melamine, in a manner analogous to the main reaction of the melamine synthesis.

The invention provides a process for preparing melamine by pyrolysis of urea in a high-pressure process, which is characterized in that urea is, optionally together with $NH_3$, fed to a melamine reactor, there converted into melamine and the is resulting offgas is taken off at the top of the reactor, the melamine melt formed is fed from the top into a cooling reactor and admixed in the cooling reactor with such an amount of urea that it is cooled to a temperature which is 1–50° C., preferably 1–30° C., above the melting point of the melamine, which is dependent on the prevailing $NH_3$ pressure, after which the $CO_2$ formed is driven out by introduction of $NH_3$ in countercurrent, the gases are separated off at the top of the cooling reactor and the melamine melt is subsequently worked up in any appropriate way.

To carry out the process of the invention, urea, which preferably comes from a urea scrubber, is introduced at a temperature of about 135–250° C. from below into a melamine reactor. Together with the urea, gaseous $NH_3$ which is both dissolved in the melt coming from the urea scrubber and can be additionally introduced, is introduced at a temperature of about 150–450° C. from below into the reactor. The molar ratio of the $NH_3$ fed to the melamine reactor to the urea fed in is 0–3 mol, preferably 0–2 mol, particularly preferably about 0–1 mol, of $NH_3$/mol of urea. The pressure in the melamine reactor is in a range of about 50–350 bar, preferably 80–250 bar.

The temperature in the melamine reactor is in a range of about 320–450° C., preferably 300–400° C., particularly preferably 330–380° C.

The urea introduced into the melamine reactor is converted into melamine, $CO_2$ and $NH_3$ in an endothermic reaction. The melamine melt produced additionally contains variable amounts of dissolved $NH_3$ and $CO_2$ and also condensation by-products and unreacted urea. Owing to the intrinsic vapour pressure of melamine, the offgas, which consists mainly of $NH_3$ and $CO_2$, additionally contains gaseous melamine.

It is possible to use any reactor or a plurality of reactors as a melamine reactor; preference is given to a tank reactor, for example a stirred tank reactor. The mixing of the reaction mixture in the stirred tank reactor can be achieved either by means of a stirrer or by means of the reaction gases formed. The heat required for the reaction can be introduced in various ways. It is preferably supplied by means of a salt melt circulating in vertical tubes, preferably double-wall tubes in the interior of a shell-and-tube reactor. Here, the salt melt usually flows in via the outer shell and flows out via the inner tube cross section. The reaction mixture is preferably mixed by natural convection resulting from the density differences between the reaction gases formed and the melamine melt. Urea and $NH_3$ are introduced together at the bottom of the reactor and converted into melamine and offgas. In the upper part of the reactor, the reaction mixture separates into offgas and liquid melamine.

While the offgas is continuously taken off at the top of the reactor, the major part of the melamine melt flows downward under the force of gravity. Owing to the fact that the reaction mixture of crude melamine and offgas has a density different from that of the crude melamine melt which has been freed of offgas, circulation takes place in the interior of the reactor. The melamine formed is discharged from the reactor via the overflow located in the upper part of the reactor. The offgas formed is passed to an offgas scrubber, while the melamine is passed to a cooling reactor where it is introduced in the upper part of the cooling reactor.

In addition to the melamine melt coming from the melamine reactor, urea is introduced into the cooling reactor in such an amount that the melamine melt is cooled to a temperature which is from 1 to 50° C., preferably from 1 to 30° C., above the melting point of the melamine which depends on the prevailing $NH_3$ pressure. This amount is usually from 1 to 5% by weight of the total amount of urea required for preparing the melamine, preferably from 2 to 3% by weight. The urea preferably comes from the offgas scrubber and accordingly contains dissolved $NH_3$. However, it is also possible to introduce virtually ammonia-free urea melt directly from the urea plant, or urea dissolved in liquid $NH_3$.

Furthermore, a small amount of water corresponding to the respective water content of industrial urea is introduced with the urea. The amount of water introduced is 0.1–5% by weight of water, preferably 0.1–3% by weight, based on urea fed in. Furthermore, fresh $NH_3$ gas is introduced and, as a result of the endothermic reaction with a decreasing temperature of the melt, the remainder of the total amount of urea is converted into melamine and offgas which once again consists mainly of $CO_2$ and $NH_3$ and traces of gaseous melamine. The quantity of heat necessary for the conversion of the remaining urea into melamine comes from the melamine melt from the melamine reactor, which is at the same time cooled to the desired temperature.

The temperature of the urea fed in is from about 135° C. to 250° C., preferably from about 170 to 220° C., and the temperature of the gaseous $NH_3$ is from about 150 to 450° C. Both materials are introduced into the cooling reactor from below in finely divided form.

The molar ratio of $NH_3$ fed to the cooling reactor to the amount of melamine present in the cooling reactor is about 0.1–10 mol, preferably 0.1–5 mol, particularly preferably 0.1–2 mol, of $NH_3$.

The pressure in the cooling reactor can be equal to, lower than or higher than the pressure in the melamine reactor. The pressure in the cooling reactor is preferably about equal to that in the melamine reactor and is in a range from about 50 to 350 bar, preferably from about 80 to 250 bar. The temperature in the cooling reactor is lower than the temperature in the melamine reactor and is usually in a range from about 300 to 350° C.

The temperature in the cooling reactor has to be selected as a function of the pressure-dependent melamine melting point so that the melamine is liquid at all times and the temperature prevailing in the reactor is preferably as close as possible to the respective melting point.

It is possible to use any reactor as a cooling reactor, for example a vertical vessel which may be provided with packing elements and is preferably filled to an extent of more than 60% with the melamine melt during operation, or a stirred reactor.

The cooling reactor can also be configured as a falling film reactor. In this case, it consists essentially of one or more tubes in which the melamine melt flows from the top downwards while gaseous ammonia is passed upwards in countercurrent through the melamine melt or over the film of melamine melt. The uniform wetting of the tubes by the descending stream of melamine results in a virtually constant thickness of the melamine film on the interior wall of the tube.

In a further embodiment, the cooling reactor is a combination reactor whose upper part is configured as a tank reactor and whose lower part is configured as a falling film reactor. In this case, it is advantageous to recirculate the gases separated off from the falling film reactor to the melamine reactor. It is also advantageous to feed the gases separated off from the falling film reactor into the tank reactor. The cooling reactor can also comprise a plurality of compartments arranged one above the other and separated from one another by trays, for example valve trays.

In the cooling reactor, the as yet unreacted urea present in the melamine melt coming from the melamine reactor is converted virtually completely into melamine and offgas. At the same time, the by-products present in the melamine melt, e.g. melem, melam, ammeline or ammelide, are converted under an $NH_3$ atmosphere into melamine in the cooling reactor.

The offgas, which consists mainly of $CO_2$. $NH_3$ and small amounts of gaseous melamine, is removed continuously at the top of the cooling reactor and either passed to the offgas scrubber or preferably recirculated to the melamine reactor. As a result of the advantageous reaction conditions in the cooling reactor, a melamine purity of up to 99% is achieved at the outlet of the cooling reactor.

If a higher purity of end product is desired, the melamine obtained in the cooling reactor can, with or without an increase in pressure and with further introduction of $NH_3$ with a simultaneous further lowering of the temperature, passed through an after-reactor. In the after-reactor, the melt temperature can be reduced further without solidification of the melamine occurring. The temperature in the after-reactor is once again from 1 to 50° C., preferably from 1 to 30° C., higher than the melting point of the melamine which depends on the prevailing $NH_3$ pressure. The pressure in the after-reactor can be up to 1000 bar, it is usually from about 100 to 500 bar, preferably from 150 to 350 bar.

Preference is given to introducing the melamine melt and $NH_3$ into the after-reactor from below and discharging the product at the top. The after-reactor comprises, for example, a column with internals which ensure uniform gas distribution and cooling of the melamine melt. Examples of such internals are packing or a static mixer. Cooling is achieved by means of the cold $NH_3$ introduced or suitable cooling devices.

The subsequent solidification of the melamine is carried out in any appropriate way, for example by depressurization of the ammonia-saturated melamine at a temperature just above its pressure-dependent melting point, by solidification in a fluidized bed or by quenching with water, with liquid or gaseous ammonia or by sublimation and subsequent desublimation from the gas phase.

Figure 1:
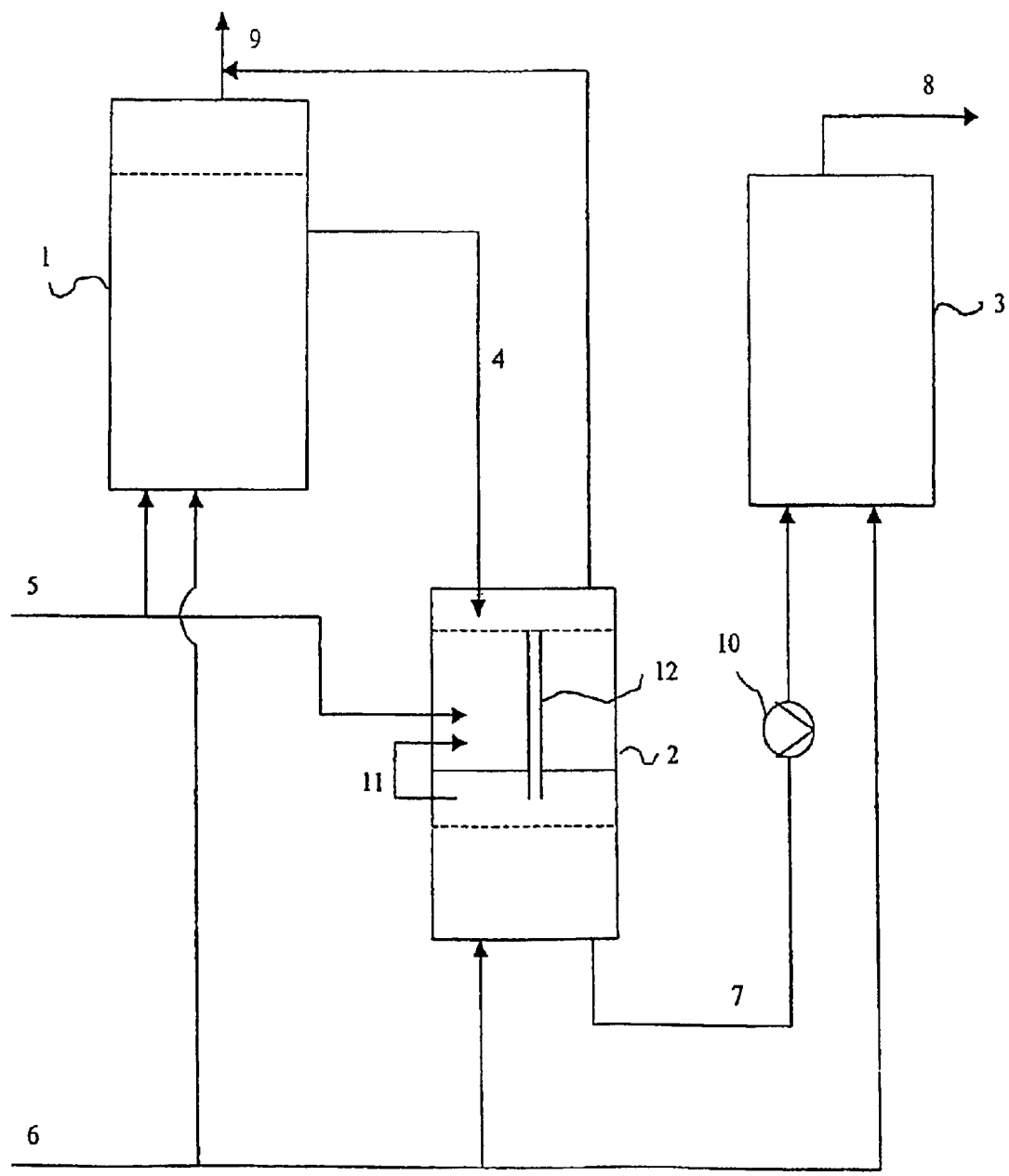
FIG. 1 schematically shows a possible arrangement for carrying out the process of the invention.

DETAILED DESCRIPTION (1) is a melamine reactor.

(2) is a cooling reactor comprising 2 compartments and having an overflow tube (12) for the melamine melt.

(3) is an after-reactor.

(4) is the melamine melt flowing from the melamine reactor into the cooling reactor.

(5) is a urea melt which is introduced both into the melamine reactor (1) and into the cooling reactor (2).

(6) is $NH_3$ gas for introduction into the melamine reactor (1) into the cooling reactor (2) and into the after-reactor (3).

(7) is the melamine melt conveyed from the cooling reactor (2) via pump (10) into the after-reactor (3).

(8) is the melamine melt coming from the after-reactor (3) for further work-up.

(9) are the offgases from the melamine reactor (1) and the cooling reactor (2).

(11) is the offgas from the lower compartment of the cooling reactor (2), which is either recirculated as stripping gas to the upper compartment of the cooling reactor (2) or to the melamine reactor (1).

EXAMPLE 4103 kg/h of melamine melt and 370 kg/h of urea are introduced from above into a cooling reactor provided with Sulzer packing, height: 4.5 m, diameter: 0.8 m, which is at a pressure of 130 bar and a temperature of 380° C. In countercurrent, 1152 kg/h of $NH_3$ gas having a temperature of 350° C. are passed through the cooling reactor from below and the gases are taken off at the top of the cooling reactor and fed to the main reactor. At the bottom of the cooling reactor, 4395 kg/h of the $NH_3$-saturated melamine melt having a purity of 99.0% and a temperature of 350° C. are taken off and passed together with 295 kg/h of $NH_3$ gas through an after-reactor provided with static mixing elements (Sulzer mixer packing), having a height of 6 m and a diameter of 0.3 m and operated at a pressure of 250 bar and a temperature of 325° C. At the outlet of the after-reactor, 4690 kg/h of an $NH_3$-saturated melamine melt are obtained. The melamine obtained has a purity of 99.6%.

What is claimed is:

1. A process for preparing melamine by pyrolysis of urea in a high-pressure process, comprising: feeding urea to a melamine reactor, converting the urea into melamine to form a melamine melt taking a resulting offgas off at the top of the reactor, feeding the melamine melt from a top of the melamine reactor via an overflow into a cooling reactors admixing the melamine melt in the cooling reactor with such an amount of urea that it is cooled to a temperature which is 1–50° C. above the melting point of the melamine, which is dependent on the prevailing $NH_3$ pressure, then driving out formed $CO_2$ by introduction of $NH_3$ in countercurrent, separating gases off at the top of the cooling reactors and subsequently working up the melamine melt.

2. The process according to claim 1, wherein 1–5% by weight of the total amount of urea required for preparing the melamine is introduced into the cooling reactor.

3. The process according to claim 1, wherein the urea introduced into the cooling reactor comes from at least one of an offgas scrubber and a urea plant.

4. The process according to claim 1, wherein the urea introduced into the cooling reactor is in the form of a solution in liquid $NH_3$.

5. The process according to claim 1, wherein the urea has a water content of 0.1–5% by weight.

6. The process according to claim 1, wherein the cooling reactor is a tank reactor.

7. The process according to claim 1, wherein the cooling reactor is a falling film reactor.

8. The process according to claim 1, wherein the cooling reactor comprises a plurality of compartments arranged one above the other.

9. The process according to claim 1, wherein the cooling reactor is a combination reactor whose upper part is configured as a tank reactor and whose lower part is configured as a falling film reactor.

10. The process according to claim 6, wherein the gases separated off from the falling film reactor are conveyed into the tank reactor.

11. The process according to claim 1, wherein the gases separated off from the cooling reactor are recirculated to the melamine reactor.

12. The process according to claim 1, wherein the melamine formed in the cooling reactor is fed to an after-reactor at a temperature which is from 1 to 50° C. above the melting point of the melamine which is dependent on the prevailing $NH_3$ pressure and is subsequently worked up in any appropriate way.

13. The process according to claim 12, wherein the temperature in the after-reactor is from 1 to 30° C. above the melting point of the melamine which is dependent on the prevailing $NH_3$ pressure.

14. The process according to claim 12, wherein the pressure in the after-reactor is from 100 bar to 1000 bar.

15. The process according to claim 14, wherein the temperature in the after-reactor is from 1 to 30° C. above the melting point of the melamine which is dependent on the prevailing $NH_3$ pressure.

16. The process according to claim 1, wherein feeding urea to a melamine reactor comprises feeding urea together with $NH_3$ to a melamine reactor.

17. The process according to claim 2, wherein 2–3% by weight of the total amount of urea required for preparing the melamine is introduced into the cooling reactor.

18. The process according to claim 5, wherein the urea has a water content of 0.1–3% by weight.

* * * * *

UNITED STATES PATENT AND TRADEMARK OFFICE
CERTIFICATE OF CORRECTION

PATENT NO. : 6,870,050 B2
DATED : March 22, 2005
INVENTOR(S) : Coufal et al.

It is certified that error appears in the above-identified patent and that said Letters Patent is hereby corrected as shown below:

Title page,
Item [57], ABSTRACT,
Lines 5 and 6, delete "C." insert -- C --.

Column 5,
Lines 16 and 22, delete "reactors", insert -- reactor, --.

Signed and Sealed this

Eighth Day of November, 2005

JON W. DUDAS
*Director of the United States Patent and Trademark Office*